(12) United States Patent
Shah et al.

(10) Patent No.: US 10,214,001 B2
(45) Date of Patent: Feb. 26, 2019

(54) RIGID STIFFENER-REINFORCED FLEXIBLE NEURAL PROBES, AND METHODS OF FABRICATION USING WICKING CHANNEL-DISTRIBUTED ADHESIVES AND TISSUE INSERTION AND EXTRACTION

(71) Applicant: LAWRENCE LIVERMORE NATIONAL SECURITY, Livermore, CA (US)

(72) Inventors: Kedar G. Shah, Oakland, CA (US); Diane George, Livermore, CA (US); Satinderpall S. Pannu, Pleasanton, CA (US); Sarah Felix, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 5 days.

(21) Appl. No.: 14/376,557

(22) PCT Filed: Feb. 4, 2013

(86) PCT No.: PCT/US2013/024673
§ 371 (c)(1),
(2) Date: Aug. 4, 2014

(87) PCT Pub. No.: WO2013/116864
PCT Pub. Date: Aug. 8, 2013

(65) Prior Publication Data
US 2014/0378993 A1 Dec. 25, 2014

Related U.S. Application Data

(60) Provisional application No. 61/594,774, filed on Feb. 3, 2012.

(51) Int. Cl.
*B32B 7/12* (2006.01)
*B32B 37/12* (2006.01)
(Continued)

(52) U.S. Cl.
CPC ...... *B32B 37/1284* (2013.01); *A61B 5/04001* (2013.01); *A61B 90/11* (2016.02);
(Continued)

(58) Field of Classification Search
CPC ... B29C 65/548; A61B 5/04001; A61B 90/11; A61N 1/05; A61N 1/0551; B32B 37/1284
(Continued)

(56) References Cited

U.S. PATENT DOCUMENTS 3,397,102 A * 8/1968 Schraub .................. B23Q 1/26
156/257
3,647,300 A * 3/1972 Skala .................... G01N 21/532
250/233

(Continued)

FOREIGN PATENT DOCUMENTS

KR 100384283000 A1 5/2003
WO WO-2009013321 A2 * 1/2009 ............ B01L 3/5027

*Primary Examiner* — John L Goff, II
(74) *Attorney, Agent, or Firm* — James S. Tak

(57) ABSTRACT

A stiffener-reinforced microelectrode array probe and fabrication method using wicking channel-distributed adhesives which temporarily adheres a flexible device onto a rigid stiffener for insertion and extraction. Assembly is by dispensing a liquid adhesive into a narrow open groove wicking channel formed on the stiffener so that the adhesive is wicked along and fills the channel by capillary action, and adhering the adhesive-filled bonding side of the elongated section of the rigid substrate to a flexible device.

5 Claims, 10 Drawing Sheets

(51) Int. Cl.
*A61B 5/04* (2006.01)
*A61N 1/05* (2006.01)
*A61B 90/11* (2016.01)

(52) U.S. Cl.
CPC .............. *A61N 1/05* (2013.01); *A61N 1/0551* (2013.01); *A61B 2562/125* (2013.01); *A61N 1/0534* (2013.01); *Y10T 156/10* (2015.01); *Y10T 428/24612* (2015.01)

(58) Field of Classification Search
USPC ........................................................ 156/305
See application file for complete search history.

(56) References Cited

U.S. PATENT DOCUMENTS

| | | | | |
|---|---|---|---|---|
| 4,019,886 A | * | 4/1977 | Hoffman | B41J 2/162 347/47 |
| 4,973,126 A | * | 11/1990 | Degani | G02B 6/3636 385/55 |
| 5,985,086 A | * | 11/1999 | Peall | B29C 65/548 156/292 |
| 6,144,425 A | * | 11/2000 | Kawabata | G02F 1/13336 349/122 |
| 6,752,490 B2 | * | 6/2004 | Pickrell | B41J 2/1429 347/68 |
| 2004/0071600 A1 | * | 4/2004 | Ono | B01L 3/5027 422/551 |
| 2004/0085174 A1 | * | 5/2004 | Decristofaro | H01F 3/14 336/178 |
| 2005/0107742 A1 | | 5/2005 | Ghovanloo et al. | |
| 2007/0123765 A1 | | 5/2007 | Hetke et al. | |
| 2009/0240314 A1 | | 9/2009 | Kong | |
| 2009/0312770 A1 | | 12/2009 | Yoshida | |
| 2010/0331935 A1 | | 12/2010 | Tabada et al. | |
| 2011/0144467 A1 | | 6/2011 | Yao | |

\* cited by examiner

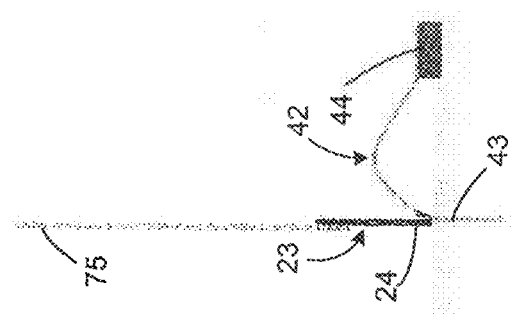
Figure 24
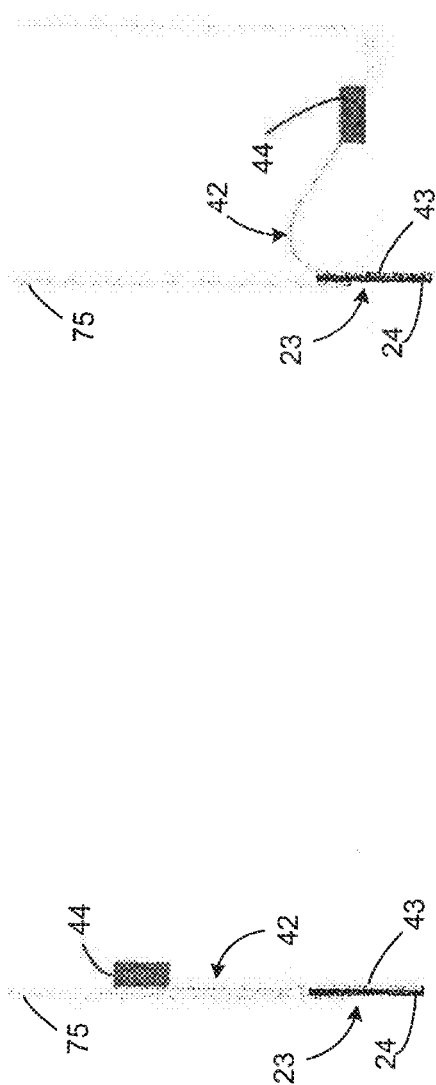
Figure 22
Figure 23
Figure 21

RIGID STIFFENER-REINFORCED FLEXIBLE NEURAL PROBES, AND METHODS OF FABRICATION USING WICKING CHANNEL-DISTRIBUTED ADHESIVES AND TISSUE INSERTION AND EXTRACTION

I. CLAIM OF PRIORITY IN PROVISIONAL APPLICATION

This patent document claims the benefit and priority of U.S. Provisional Application No. 61/594,774, filed on Feb. 3, 2012, hereby incorporated by reference.

II. FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

III. FIELD OF THE INVENTION

The present invention relates to the field of thin film microprobes and fabrication methods, and more particularly to flexible microelectrode array probes having rigid stiffeners permanently or temporarily adhered using wicking channel-distributed adhesives, to provide structural reinforcement to resist bending and buckling, especially during insertion.

IV. BACKGROUND OF THE INVENTION

Micro-electrode neural probes are essential tools in neuroscience. They provide a direct electrical interface with the neurons of a biological entity's nervous system to stimulate and/or record neural activity. Such neural probes enable researchers and clinicians to better explore and understand neurological diseases, neural coding, neural modulations, and neural topologies, and ultimately treat debilitating conditions of the nervous system, such as for example depression, Parkinson's disease, epilepsy, and deafness.

To enable interaction with neurons, however, neural probes must be sufficiently rigid to penetrate neutral tissue during surgical implantation. One common method is to construct neural probes using a rigid/stiff material, such as silicon. In this method, electrodes and their leads are microfabricated on the silicon shank, with layers of trace metals separated by layers of insulating materials to create the device. FIG. 1 shows a perspective view of a common silicon-based microelectrode array neural probe, generally indicated at reference character 10, and illustrating its basic component features. The neural probe has an elongated probe body with a silicon substrate base, an insertion end 12 (and pointed insertion tip), a connector end 13 (shown as a wide-area tab section), a top surface 15, and an opposite bottom surface 14. A plurality of electrodes 16 is exposed through the top surface at the insertion end 12, and a plurality of corresponding connector leads/pads 17 at the tab section 13 is also shown exposed through the top surface 15, and metal traces (not shown) run from the electrodes along the length of the probe and terminating on the pads which may be attached to an electrical connector (not shown). A dielectric material insulates the metal traces, electrodes and connector/contact pads. And the stiffener length depends on the insertion depth of the probe, and the wider tab on the stiffener allows for handling.

The stiffness of silicon-based neural probes, however, can have several limitations. After insertion and implantation, any movement at the probe's end can cause localized tissue damage at the probe's tip due to the probe's stiffness. Modeling and experimental studies of the interaction between microelectrode probes and neural tissue have suggested that one mechanism for degradation is micro-tearing of neural tissue due to slight relative motion between the probe and tissue. Thus, a major challenge for implanted silicon-based neural probes in particular is stability and longevity of the stimulation and recording functions.

An alternative to rigid neural probes is to fabricate flexible probes that match more closely the bulk stiffness properties of neural tissue in order to minimize relative micromotion. Biocompatible thin film polymers such as polyimide and parylene have been adopted as favorable substrates for microelectrode probes. If instead neural probes are fabricated on a flexible polymer, the device causes less tissue damage by bending along the contours of the tissue. The substrate of the microelectrode array may be made flexible by utilizing thin-metal electrode sites and enclosing the wiring between polymer materials. The resulting electrode array is completely flexible, thereby providing needed strain relief. FIG. 2 shows schematic and enlarged views of an example flexible neural probe 20 known in the art, also showing a plurality of electrodes at an insertion section 21, and corresponding connector pads 22 at an opposite wide-area tab section. Such flexible neural probes may be microfabricated using a multi-stack layer of polymer (such as, but not limited to polyimide, parylene, and silicone). Metal traces and electrodes are patterned on the polymer, and subsequent layers of polymer are deposited to encapsulate the device. Multiple metal layers are connected between polymer layers using a series of lithography and etching steps.

Though flexibility is advantageous for chronic implantation and use, flexible neural implants alone are often not stiff enough to penetrate neural tissue during surgical implantation. Flexible neural probes are often stiffened to aid in insertion and implantation. Stiffening flexible neural probes may take various forms, such as coating flexible tips in dissolvable material, and manually adhering wires onto flexible tips. Because flexible probes are difficult to insert into neural tissue, an incision is usually first created to effect implantation. This typically results in increased tissue damage. Still other example approaches are disclosed in U.S. Pat. Pub. No. 2005/0107742 disclosing a shatter-resistant microprobe, and U.S. Pat. Pub. No. 2009/0299166 disclosing a MEMS flexible substrate neural probe. And other various approaches to facilitate insertion of flexible probes while preserving the desirable mechanical properties are also known. For example, one class of designs modifies the polymer probe geometry to increase stiffness in certain sections or axes while maintaining compliance in other parts. This has been accomplished by incorporating ribs or layers of other materials.

In order to stiffen flexible neural probes to aid in insertion and implantation, rigid substrates may also be attached directly to the probes using adhesives. In this method, a metal wire is adhered to the tip of a flexible neural probe in order to stiffen the device upon insertion (see FIG. 3). Superglue is the adhesive of choice and is applied by hand. This method has several limitations, in addition to those listed under the first method of the silicon only stiffener. For example, hand-gluing the wire and probe tip together is a difficult and time-intensive technique. Superglue is difficult to control and, if comes in contact with electrodes, will damage the device. Moreover, once attached, the stiffening wire is permanently attached and cannot be removed from the body or the device.

Another approach integrates a 3-D channel into the polymer probe design that is filled with biodegradable material [9]. This probe can be temporarily stiffened, and after insertion the material in the channel dissolves and drains out. However, methods such as these that permanently modify the geometry of the final implanted device may compromise some of the desirable features of the flexible probe.

Another method of stiffening a flexible neural probe, but does not alter the final probe geometry, is by coating the polymer probe with a stiffening material, and in particular a biodegradable (i.e. dissolvable) stiffening material to temporarily stiffen the device [10-12]. However, typical biodegradable materials have Young's moduli orders of magnitude smaller than that of silicon and would consequently require larger thickness to achieve the same stiffness. Adequately coating the probe can result in a more rounded or blunt tip, making insertion more difficult. Also, since dissolvable coatings are exposed, there is a risk of them dissolving immediately upon contact, or even close proximity, with the tissue. Dissolvable materials may include, for example, sucrose or PLGA, to improve the modulus of elasticity of the device. Neural probes are dipped into a material and left to dry or cure. Additional coating may be applied to improve strength and ease of insertion. This method has several limitations as well. The dissolvable material may not have a large enough modulus of elasticity to easily implant device into neural tissue, as demonstrated in FIG. 4. When coating entire probe tip, film forms over the electrodes, possibly making the device unusable. Finally, coating the probe leads to rounding of the tip, making insertion more difficult and destructive to tissue.

Yet another class of methods uses novel probe substrate materials that reduce in stiffness after being implanted into tissue. Such materials include shape memory polymers [13] and a mechanically adaptive nanocomposite [14]. These materials are able to decrease in elastic modulus significantly after insertion, and can result in probes that more closely match the mechanical properties of neural tissue. However, the achievable range of stiffness is still limited, so they may not be able to provide very high stiffness equivalent to silicon or tungsten wires. Thus in the case of flexible probes that are very long (e.g. >3 mm.) or that have extremely low stiffness, a method of temporarily attaching a more rigid stiffener may still be required.

What is needed is a method of inserting/implanting a flexible microelectrode array probe while maintaining its flexibility. Furthermore, it would be advantageous to provide a microelectrode array probe capable of mitigating tissue damage during implantation, and that also can be relatively easily and efficiently fabricated in large numbers.

V. SUMMARY OF THE INVENTION

One aspect of the present invention includes a method of assembling a rigid substrate onto a flexible device comprising: providing a rigid substrate (i.e. stiffener) having an elongated section, and a narrow open groove channel formed on a bonding side of the elongated section; dispensing a liquid adhesive into the narrow open groove channel so that the adhesive is wicked along and fills the narrow open groove channel by capillary action; and adhering the adhesive-filled bonding side of the elongated section of the rigid substrate to a flexible device.

Another aspect of the present invention includes a method of assembling a rigid substrate onto a flexible device comprising: providing a rigid substrate (i.e. stiffener) having an elongated section, a narrow open groove (i.e. furrow-like) channel formed on a bonding side of the elongated section, a tab section connected to the elongated section, and a reservoir cavity formed on the tab section that is in fluidic communication with the narrow open groove channel; aligning and positioning a flexible device against the bonding side of the elongated section to cap the narrow open groove channel with the flexible device and thereby form a narrow enclosed groove channel that is in fluidic communication with the reservoir cavity at one end and having an exit opening (e.g. weep hole) at an opposite end; and dispensing a liquid adhesive into the reservoir cavity so that the adhesive is wicked along and fills the narrow enclosed groove channel by capillary action to adhere the rigid substrate to the flexible device.

Another aspect of the present invention includes a flexible device stiffener, comprising: a rigid substrate with an elongated section, and a narrow open groove channel formed on a bonding side of the elongated section and capable of wicking a liquid adhesive along the narrow open groove channel to fill the narrow open groove channel by capillary action, whereby upon filling the narrow open groove channel with a liquid adhesive by capillary action, the adhesive-filled bonding side of the elongated section may be adhered to a flexible device to stiffen said flexible device.

Another aspect of the present invention includes a rigid substrate-backed flexible device, comprising: a rigid substrate (i.e. stiffener) with an elongated section, and a narrow open groove channel formed on a bonding side of the elongated section; a flexible device aligned and Positioned against the bonding side of the rigid substrate to cap the narrow open groove channel into a narrow enclosed groove channel that has an inlet opening at one end and an exit opening (e.g. weep hole) at an opposite end; and an adhesive wicked into the narrow open channel or narrow closed channel that adheres the rigid substrate to the flexible device so as to stiffen said flexible device.

Another aspect of the present invention includes a method of inserting an elongated flexible probe in a probed medium, comprising: providing a probe assembly having: an elongated flexible probe having a connector end, an opposite insertion end, and an insertion section terminating at the insertion end; an electronics connector connected to the connector end; and a rigid substrate having an insertion shank/stiffener, a tab connected to the insertion shank/stiffener, and a narrow open groove channel formed on a bonding side of the insertion shank/stiffener and filled with a reversible adhesive, said insertion section aligned and positioned against the narrow open groove channel so that the reversible adhesive temporarily adheres the insertion section to the insertion shank/stiffener; affixing the tab section to an end of a rigid base so that the insertion shank/stiffener and the insertion section extend below the end of the rigid base; attaching the electronics connector to the rigid base; controlling the rigid base to insert the insertion shank/stiffener and the temporarily adhered insertion section into the probe medium; transferring the electronics connector to a surface of the probed medium; detaching the insertion section from the insertion shank/stiffener; controlling the rigid base to remove/extract the insertion shank/stiffener from the probed medium whereby the detached insertion section remains in the probed medium.

Generally, the present invention is directed to a method in which the flexible probe is temporarily or permanently attached to a rigid body stiffener with a liquid adhesive that securely holds the probe during insertion. The stiffener is formed with wicking channels which exploit capillary action to distribute a liquid adhesive along the entire length of the probe to ensure uniform adhesive coverage, accurate and repeatable alignment, no overflow of adhesive to the functional side of the probe, and ultimately strong adhesion.

Moreover, with a temporary biodissolvable adhesive material (such as for example biodissolvable polyethylene glycol (PEG) the adhesive material dissolves after being inserted into the tissue, and the stiffener is extracted while the probe remains implanted to restore the probe to its intended flexibility. In addition to the assembly process, we present the method of implementing the removable stiffener during surgery, as well as an in vitro procedure to evaluate extraction of the stiffener.

In many microsystems applications, it is critically important to precisely and accurately align and attach two substrates to each other using permanent or temporary adhesives. At the millimeter and micron scales, the accuracy of attachment is largely dependent on the amount and coverage of adhesive dispensed. Excess adhesive can overflow from the bond interface and damage the substrates, while inadequate adhesive creates a non-uniform bond. The present invention provides a method for consistently and uniformly dispensing adhesive on a substrate (e.g. stiffener), to attach it to another substrate (e.g. flexible probe) with precision and accuracy in all spatial dimensions (length, width, height).

In particular, this invention describes the use of a wicking channel to use capillary force to distribute a precise amount of adhesive along the length of the stiffener substrate prior to neural implant assembly. First, single or multiple channels (e.g. inter-connected channels) are created in a pattern that covers the areas that need to be attached. Second, a controlled amount of adhesive is dispensed into the channel or channels, which wicks along the channel using capillary forces to evenly coat and fill the channel. Alternately, the adhesive may be dispensed into a containment reservoir fluidically connected to the channel or channels. Finally, the two substrates (e.g. stiffener and flexible probe) are aligned and attached using a tool such as a flip-chip bonder which allows precise positioning in the lateral dimensions. The adhesive may be cured using a combination of temperature, pressure, light, and/or time. A stiffener design having wicking channels allows for uniform distribution of the PEG adhesive along the length of the probe. Flip-chip bonding, a common tool used in microelectronics packaging, enables accurate and repeatable alignment and attachment of the probe to the stiffener. The probe and stiffener are surgically implanted together, then the PEG is allowed to dissolve so that the stiffener can be extracted leaving the probe in place.

There are multiple advantages to the assembly methods and wicking-channel stiffener designs described in the embodiments of the present invention. Dispensed adhesive can be easily controlled. A pneumatic dispenser can precisely and repeatedly dispense the necessary amount of material for wicking, eliminating the chance of adhesive overflow. The reservoir and channel shapes can be optimized for uniform and controlled delivery of adhesive. Many types of adhesive with an appropriate viscosity can be applied into the reservoir of the stiffener and be wicked successfully. Adhesives of different bonding strengths can be tested. Bio-dissolvable adhesive can be used, which allows the stiffener to be removed from the tissue after the adhesive has dissolved. This technique is ideal for long-term implantation. In one embodiment of a temporary reversible adhesive, polyethylene glycol (PEG) is used, wherein the repeatable melting and solidification of the material is exploited to facilitate the assembly process using the wicking stiffener. First, micro-pellets of PEG are generated by melting some of the material on a surface on which the PEG exhibits hydrophobic behavior. Then the material is drawn or spread to create separate droplets of a desired size. The droplets are cooled and solidify into pellets. Pellets of the desired size (volume) can then be picked and placed onto the reservoir or channel on the tab portion of a wicking stiffener. After the pellet is satisfactorily placed, the stiffener is placed on a hot plate, where the PEG melts and wicks into the channel. The stiffener is cooled when wicking is complete, and the PEG solidified again. The stiffener can then be easily aligned to the probe without the risk of wet adhesive transferring to other surfaces in the process. Once aligned and placed, the assembly is heated again to distribute the PEG, and finally cooled to complete the assembly.

In this manner, microelectrode arrays for neural interface devices that are made of biocompatible thin-film polymer are expected to have extended functional lifetime because the flexible material may minimize adverse tissue response caused by micromotion.

VI. BRIEF DESCRIPTION OF THE DRAWINGS

The accompanying drawings, which are incorporated into and form a part of the disclosure, are as follows:

FIGS. 21-24 illustrate an example progression of inserting a flexible microelectrode array into a target using a rigid body stiffener, and subsequently extracting the stiffener only.

VII. DETAILED DESCRIPTION

Figure 1:
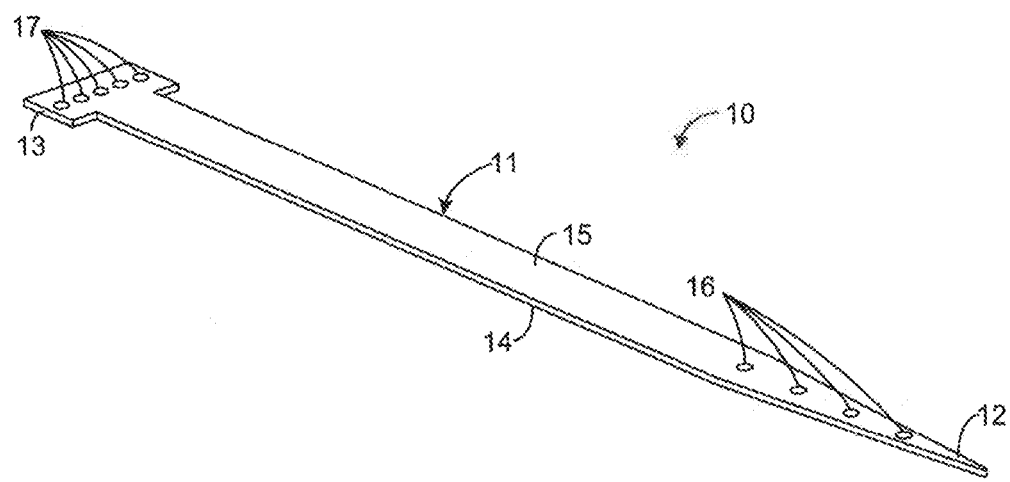
FIG. 1 is an perspective view of a common rigid-body microelectrode array probe known in the art, such as made from silicon, and illustrating the multi-electrode probe construction.
Figure 2:
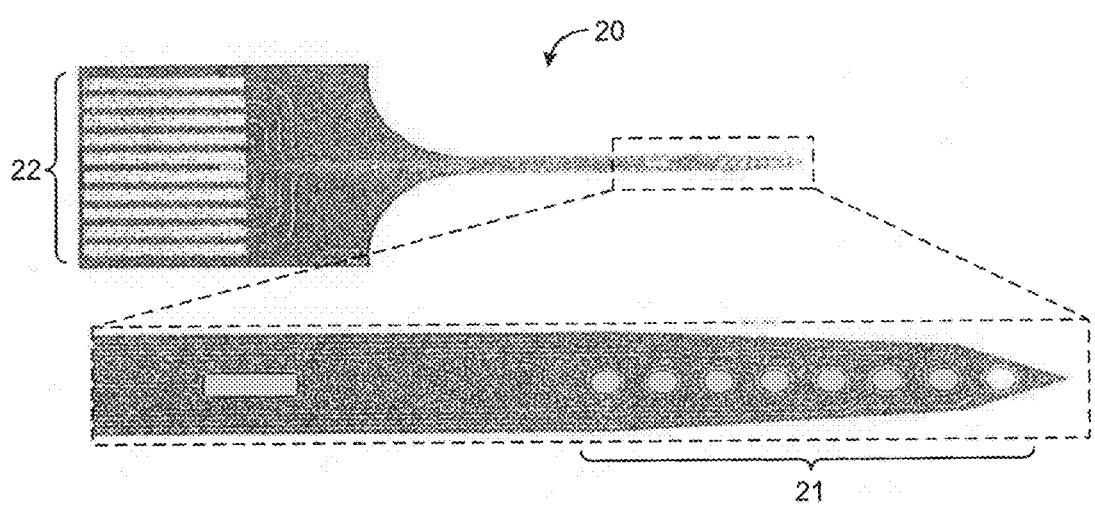
FIG. 2 is a schematic and enlarged view of an example flexible microelectrode array neural probe construction known in the art.
Figure 3:
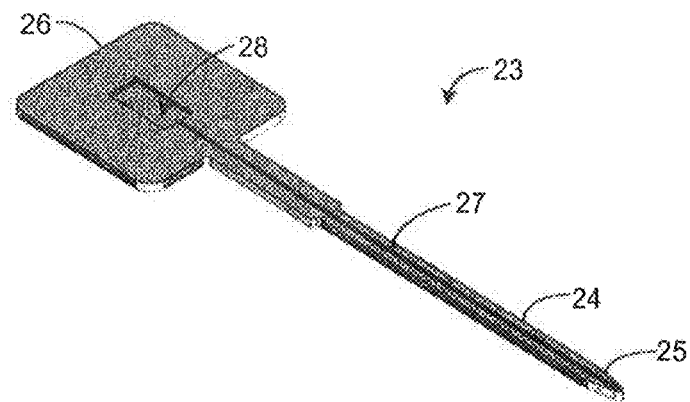
FIG. 3 is a perspective view of an example embodiment of the rigid body stiffener of the present invention illustrating a single wicking channel.
Figure 4:
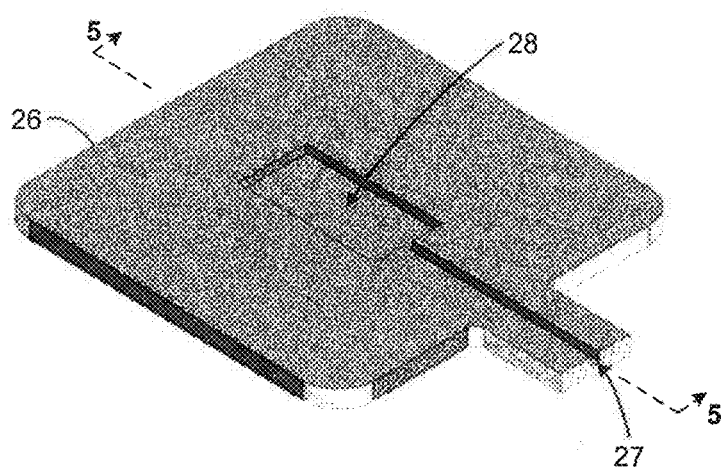
FIG. 4 is an enlarged perspective view of a mounting end or tab portion of other rigid body stiffener of FIG. 3 illustrating the reservoir cavity.
Figure 5:
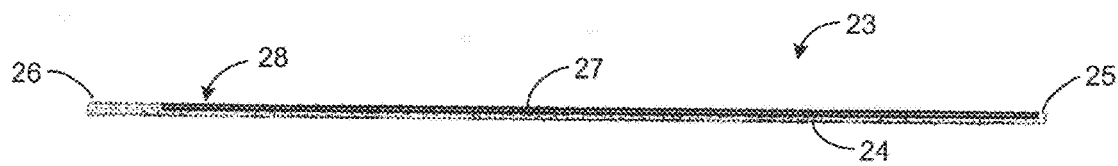
FIG. 5 is a cross-sectional view taken along line 5-5 of FIG. 4.
Figure 6:
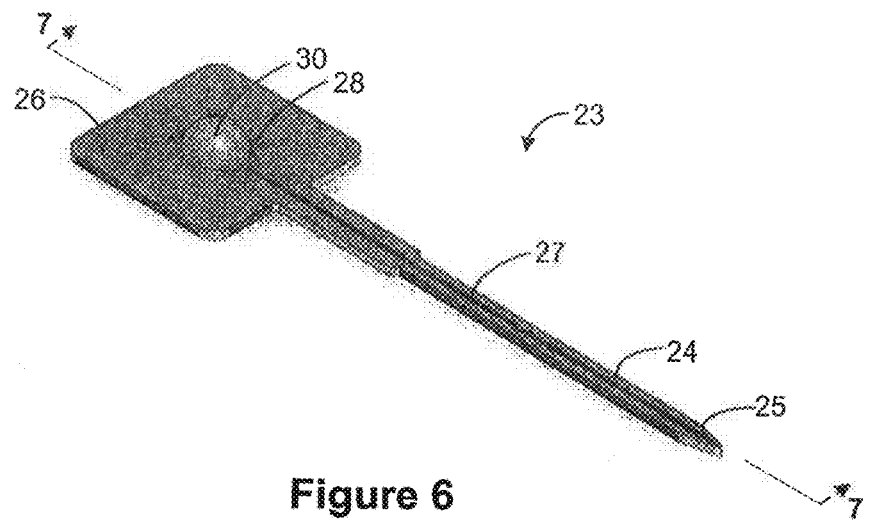
FIG. 6 is a perspective view of the rigid body stiffener of FIG. 3, shown with an adhesive droplet deposited in the reservoir cavity.
Figure 7:
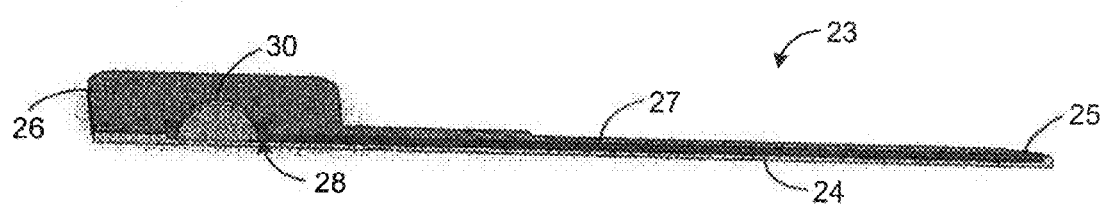
FIG. 7 is a cross-sectional view taken along line 7-7 of FIG. 6.

Turning now to the drawings, FIGS. 3-5 show an example embodiment of the rigid body stiffener of the present invention, generally indicated at 23, and having a single wicking channel 27. The stiffener may be characterized a rigid substrate, backing, or other reinforcement or support, and has an elongated insertion section 24 that extends between an insertion tip 25 and an opposite tab section 26. A reservoir cavity 28 is formed in a tab section 26 which is fluidically connected to a narrow, open-groove, wicking channel 27 extending substantially the length of the elongated insertion section 24. In particular, the reservoir cavity 28 and the wicking channel 27 are both shown formed on the same side of the stiffener 23 (i.e. the top side), where the reservoir is shown as an open cavity that is open from the top side. It is appreciated that as shown in the FIG. 3, the top side is the bonding side of the stiffener because it's the side that, due to the wicking channel being open form the top side, will bond to the flexible probe.

It is appreciated that the stiffener may be made of various types of rigid materials, including for example silicon, glass, ceramic, metal, etc. It is appreciated that some embodiments may not include a tab section or a reservoir cavity that is fluidically connected to the elongated section and the wicking channel. It is appreciated that in such cases, adhesives may be deposited directly in the wicking channel to be distributed in the channel by capillary action. Furthermore, various thin film MEMS fabrication methods (e.g. photolithography) may be employed to fabricate the structure of the stiffener, including the reservoir cavity and the wicking channel. The reservoir is on a wider tab region that facilitates handling.

Figure 15:
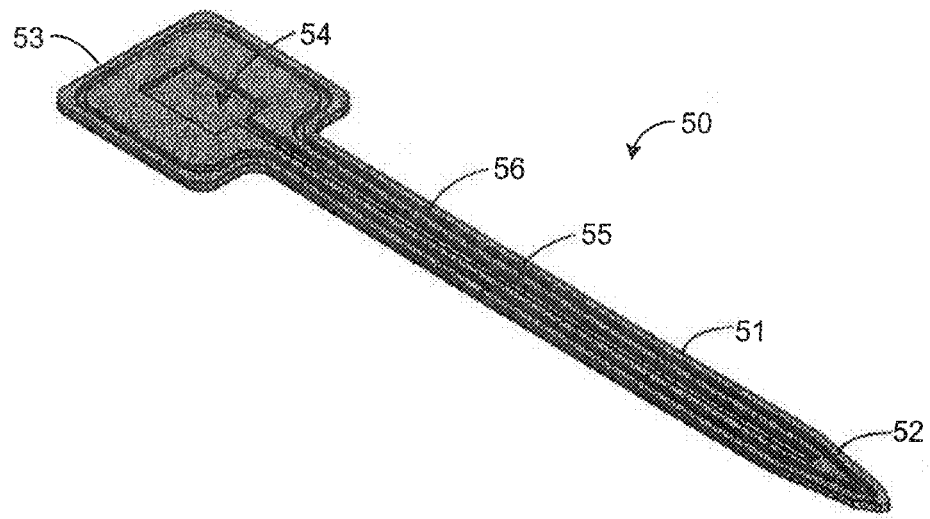
FIG. 15 is a perspective view of a second preferred embodiment of the rigid body stiffener of the present invention, illustrating source and drain channels for the wicked adhesive.

FIG. 15 is a perspective view of a second preferred embodiment of the rigid body stiffener of the present invention, generally indicated at 50, illustrating source and drain channels for the wicked adhesive. Similar to FIG. 3, the stiffener has an elongated insertion section 51 that extends between an insertion tip 52 and an opposite tab section 53. A reservoir cavity 54 is formed in the tab section which is fluidically connected to a narrow wicking channel 55 extending substantially the length of the elongated insertion section 51 to cover an attachment area. In particular, the reservoir cavity 28 and the wicking channel 27 (or source channel) are both shown formed on the same side (i.e. top side) of the stiffener 23, where the reservoir is shown as an open cavity with a top-side opening (i.e. receiving end). Furthermore, an additional drain channel 56 is provided at a radially outer position from the wicking channel 55. For low-viscosity adhesives, the wicking (source) and drain channels can be implemented to more precisely control adhesive coverage and to contain excess adhesive. In this design, the drain channel 56 surrounds (and is not connected with) the central wicking channel 55 into which adhesive is dispensed. Initially, when wicking is complete from the reservoir cavity, the source channel 55 will contain all the adhesive, and the drain channel will be empty. During the attachment process, however, the adhesive will wick between the interface of the neural probe and the stiffener i.e. between the neural probe and an interface surface of the stiffener adjacent the wicking channel 55. However, all excess adhesive will get pulled into the drain channel, preventing overflow of adhesive that could damage the neural probe.

Figure 16:
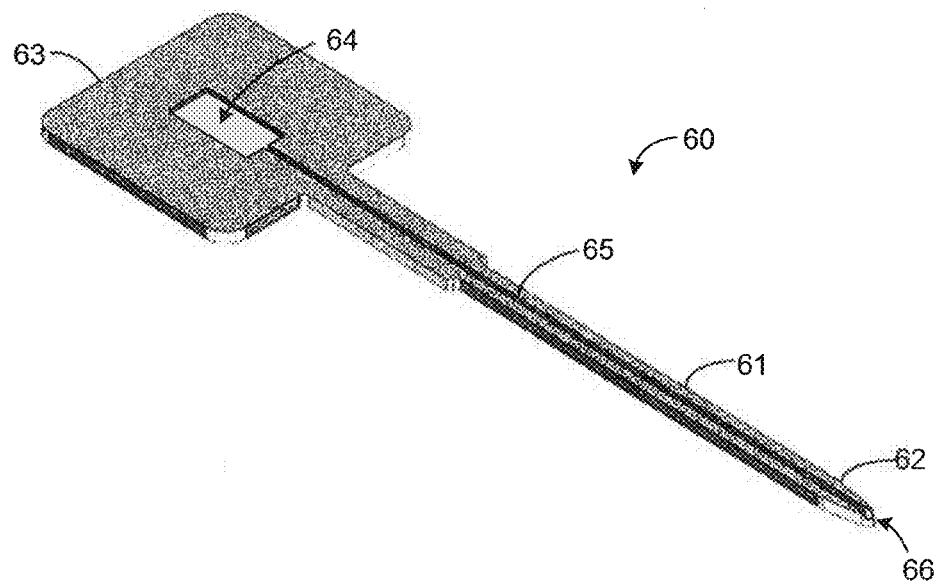
FIG. 16 is a perspective view of a third preferred embodiment of the rigid body stiffener of the present invention, having a reservoir cavity that is an open cavity that extends through the top and bottom surfaces of the tab section of the stiffener.

FIG. 16 is a perspective view of a third preferred embodiment of the rigid body stiffener of the present invention, indicated at 60, having an elongated insertion section 61 that extends between an insertion tip 62 and an opposite tab section 63. A reservoir cavity 64 is formed in the tab section 63 which is fluidically connected to a narrow wicking channel 65 extending substantially the length of the elongated insertion section 61 to cover an attachment area. In particular, the reservoir cavity 64 and the wicking channel 27 are both shown formed on the same side (i.e. top side) of the stiffener 60, where the reservoir is shown as an open cavity that extends through the top and bottom surfaces of the tab section 63 of the stiffener. In this embodiment, a "reverse wicking stiffener" is implemented with permanent or temporary adhesives. In this design, the reservoir extends all the way through the top and bottom surfaces of the stiffener. During assembly, the stiffener is first aligned and positioned against (e.g. placed on) the flexible probe, that is, the flexible device is aligned and position against and interface surface of the bonding side of the elongated section, so as to cap the narrow open groove channel with the flexible device. Capping the narrow open groove channel forms a narrow enclosed groove channel that is in fluidic communication with the reservoir cavity at one end and having an exit opening (e.g. weep hole) at an opposite end. After placement, a controlled amount of adhesive is dispensed into the reservoir from the back-side of the stiffener. Since the reservoir and channel are connected, the adhesive will wick through the reservoir, into the channel, and ultimately into the interface between the flexible neural probe and the stiffener (i.e. between the neural probe and the interface surface of the bonding side of the stiffener), thus attaching the two together to form a stiffened neural probe.

Figure 8:
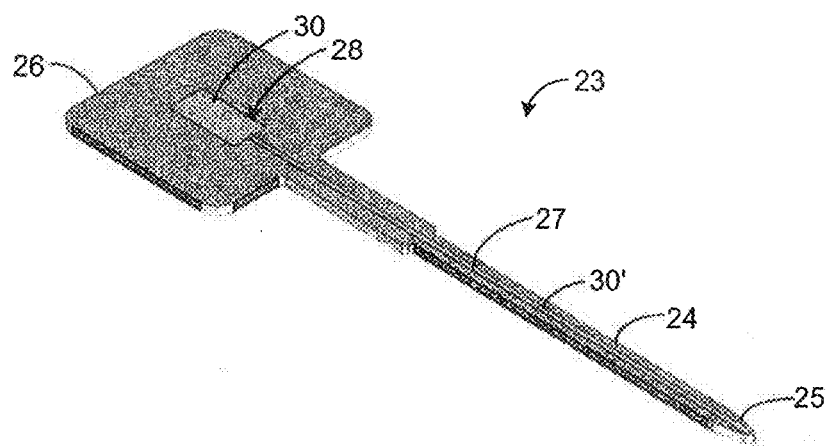
FIG. 8 is a perspective view of the rigid body stiffener following FIG. 6, and illustrating the adhesive after being distributed in the wicking channel.

FIGS. 6-14 show an example method of assembling a flexible probe to the stiffener 23 of FIGS. 3-5. In particular, a liquid adhesive 30 is shown deposited in the reservoir cavity 28. Due to capillary action, the adhesive 30' is shown in FIG. 8 wicked into the wicking channel 27 extending down to the insertion end 25. The shallow wicking channel 27 running along its length is used to distribute liquid adhesive during assembly. The wider portion of the stiffener is a tab for handling during assembly and surgical insertion. A reservoir on the tab connects to the channel. In particular, adhesive is shown dispensed into a containment reservoir located on the tab of the stiffener, and wicks using capillary force to fill the channels. (Note: in some embodiments not including a reservoir, adhesive may be dispensed directly into the channel or channels and wicked to fill said channel(s).) A precise volume of adhesive is dispensed using a pneumatic dispensing system, a calibrated syringe, or other volume-controlled method. Sufficient time is given for the adhesive to wick along the channel, and may be aided by heating the adhesive, since many liquids have the property of decreasing viscosity at elevated temperatures. Once the adhesive has wicked uniformly, it is ready to be adhered to the neural probe.

For the described attachment processes, the adhesive may be permanent (i.e. irreversible adhesive), such that the probe and stiffener are permanently bonded to each other. Alternately, a reversible, adhesive, such as a bio-dissolvable, bio-soluble, bio-degradable, or similar viscous adhesive may be used to create a temporary bond between the flexible probe and the stiffener. In this case, the reversible adhesive is removed after surgical implantation which enables removal of the stiffener so that only the flexible polymer probe stays in the body. An example of such a device, is to use an adhesive that dissolves or otherwise loses its adhesive properties when exposed to the environment of the tissue in a body. Specific examples of these adhesives include, but are not limited to agar, gelatin, glycerol, sucrose, polyethylene glycol (PEG) of various molecular weights, poly(lactic-co-glycolic acid) (PLGA), rice glue, dextran glue, dextrin, fibrin sealant, corn syrup, etc.

There are a number of variables in the design of both the insertion stiffener and the bond interface that affect the ability of a stiffener to be extracted cleanly, without having a negative impact on the integrity or placement of the flexible probe. Moreover, the existence of wicking channels in the stiffener may, in some cases, can contribute to a well-engineered interface. Some of the possible design variables are listed below:

Adhesive material: the type of material used as the dissolvable adhesive can determine factors such as dissolution time, bond strength, bond thickness, ease of assembly, and the sliding resistance between the probe and the stiffener after the adhesive dissolves.

Bond thickness: the thickness of the dissolvable adhesive layer may affect the success of extraction by determining the separation gap between the flexible device and the stiffener. Bond thickness can be controlled by type of adhesive, molecular weight of the adhesive, and method of application.

Bond uniformity: the uniformity of the coverage and thickness of the dissolvable adhesive may promote clean extraction by reducing sliding resistance between the probe and the stiffener.

Wicking channel geometry: the existence of wicking channels may affect dissolution of the adhesive. For example, channels may promote transport of PBS through the interface, but they also increase the total amount of adhesive that needs to be dissolved. Channels also affect the bonded contact area between the flexible probe and the stiffener. Importantly, as discussed in the previous section, channels facilitate distribution of the adhesive during assembly, and therefore could impact bond thickness and uniformity.

Surface roughness: surface roughness of the stiffener and/or device may affect the dissolvable bond and extraction of the stiffener.

Figure 9:
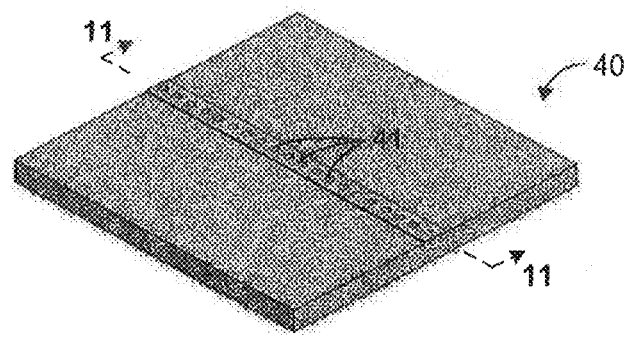
FIG. 9 is a perspective view of an exemplary assembly pedestal used for assembling the rigid body stiffener to an insertion portion of a flexible microelectrode array probe, and shown having suction ports.
Figure 10:
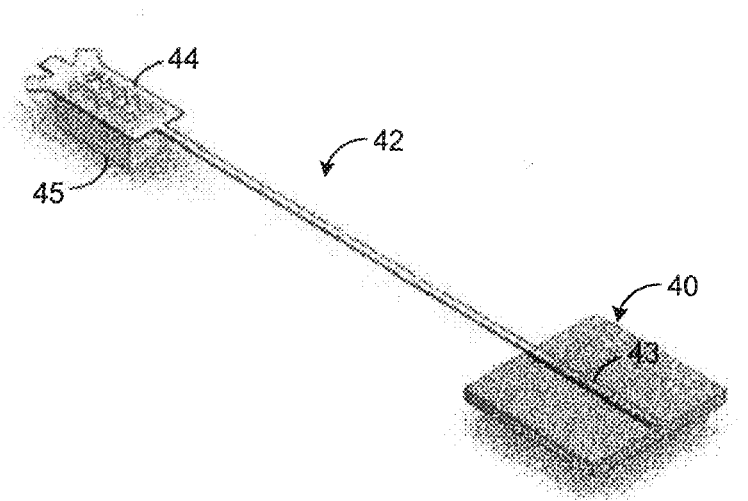
FIG. 10 is a perspective view of a flexible microelectrode array probe supported by and held against the assembly pedestal.
Figure 11:
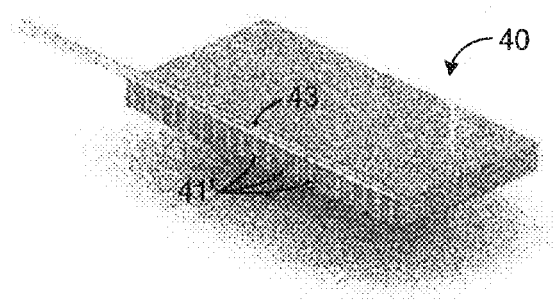
FIG. 11 is a cross-sectional view of the assembly pedestal and microelectrode array probe of FIG. 10, illustrating the suction port cavities.
Figure 12:
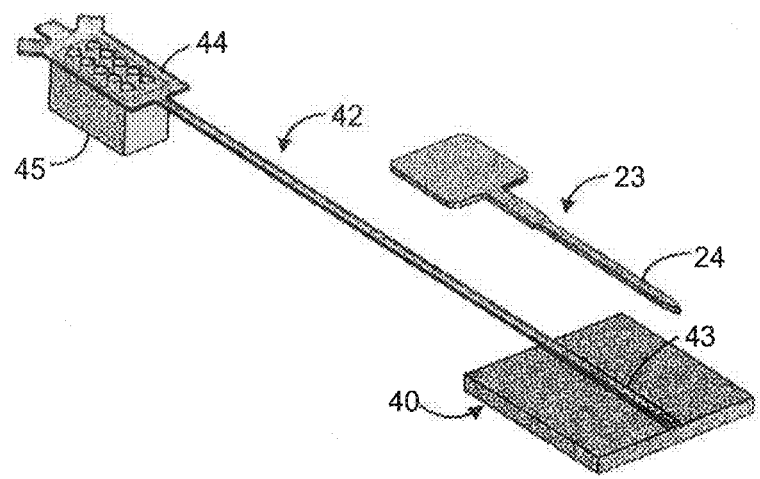
FIG. 12 is an exploded perspective view of the rigid body stiffener of FIG. 8 flipped and ready to be assembled on and adhered to the flexible microelectrode array probe supported on the assembly pedestal.
Figure 13:
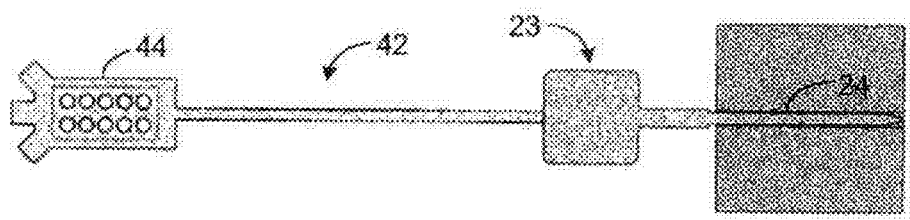
FIG. 13 is a top view of the adhered stiffener and flexible microelectrode array assembly, with the stiffener shown on top of the probe.
Figure 14:
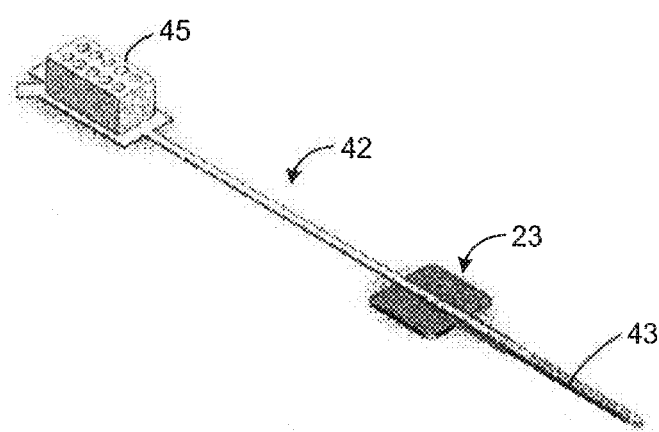
FIG. 14 is a perspective view of the adhered stiffener and flexible microelectrode array assembly of FIG. 13, with the stiffener shown below the probe.

In FIG. 9, a vacuum pedestal or assembly base 40 is shown for holding the flexible neural probe in place during assembly. The pedestal is shown having a plurality of vacuum ports 41 which hold the probe by a suction force. As shown in FIG. 11, the vacuum ports 41 communicate with vacuum channels 41' which may be connected to a vacuum source (not shown). In any case, in FIG. 10, a flexible electrode array neural probe 42 is shown aligned and positioned on the pedestal 43 with its insertion section held in place by suction. The probe 42 also has a connector 45 at the connector end 44 which may be adapted to other electronic devices. In FIG. 12, the neural probe may be aligned is shown being attached to the stiffener 23. For this, a flip-chip bonder (or similar tool) may be used to flip the stiffener 23 as shown, that allows for aligning, placing, and curing the adhesive. It is appreciated that the adhesive may be pre-cured on the stiffener in order to increase viscosity, and reduce the chance of adhesive overflow during attachment. Finally, as shown in FIGS. 13 and 14, the adhesive-filled bonding side of the elongated section of the rigid substrate/stiffener is placed onto the neural probe 42 and the adhesive is cured with a combination of heat, pressure, light, and/or time.

Figure 17:
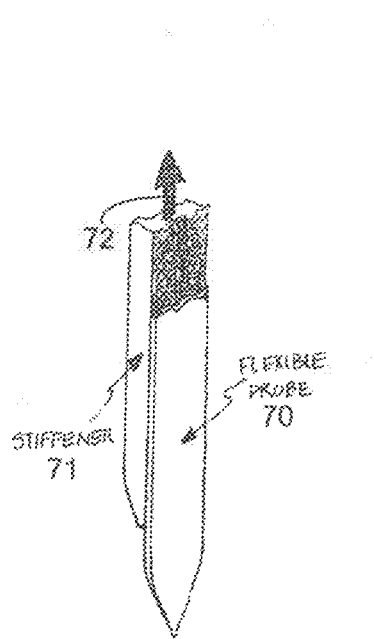
FIG. 17 is a perspective view of an exemplary removal process for removing the stiffener after implanting a flexible probe.

FIGS. 17-29 show various methods of inserting the stiffener-reinforced flexible neural probe and subsequently extracting the stiffener, such as generally shown in FIG. 17 showing a stiffener separated and removed from a flexible probe 70 by force 72. In the present invention, a common technique of inserting stiffened neural probes is augmented to facilitate removal of a temporary stiffener with wicking channels attached with biodissolvable adhesive. (Biodissolvable adhesives include, but are not limited to agar, gelatin, glycerol, sucrose, polyethylene glycol (PEG), poly(lactic-co-glycolic acid) (PLGA), rice glue, dextran glue, dextrin, fibrin sealant, corn syrup, etc.) Typically, a stereotaxic frame with micromanipulator is used to guide neural probes into position at a desired angle, and insert the probes at a controlled rate. Then, the neural interface assembly, which includes the probe and connector hardware is secured into place using dental cement or other means. In the case of a removable stiffener, the proposed procedure addresses 1) location of the connector throughout the insertion and extraction process, 2) dissolution of the adhesive, and 3) removal of the stiffener from the tissue.

Figure 18:
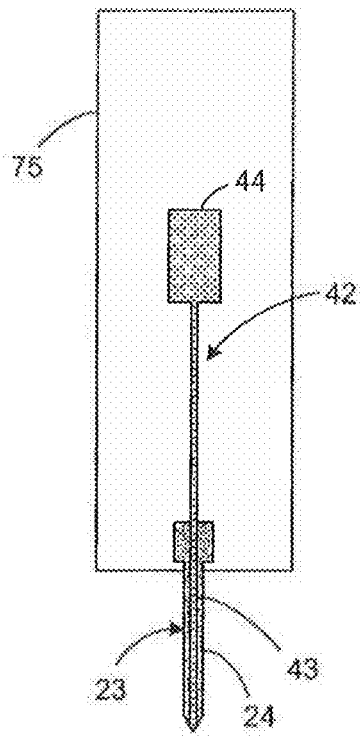
FIG. 18 is a schematic view of an example assembly for inserting a flexible microelectrode array probe with a temporarily adhered stiffener.
Figure 19:
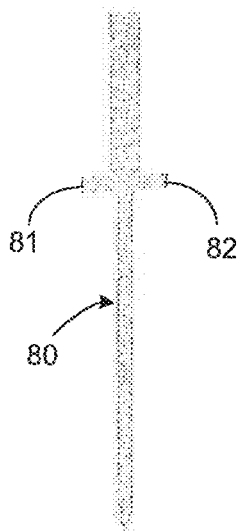
FIG. 19 is a schematic view of an example insertion section of a flexible microelectrode array probe of the present invention having anchoring arms.

FIG. 18 shows an example set up for insertion and extraction of the stiffener-reinforced flexible probe assembly. In particular, the tab section of the stiffener 23 is shown fixedly connected to glass plate 75 at a lower end thereof. The stiffener is adhered (such as by wicking-channel distributed adhesive) to an insertion section 43 of the flexible probe 42, shown also having a connector end 44 temporarily connected to the glass 75. The glass plate 75 may be mounted on a micromanipulator arm of a stereotaxic frame (not shown). In particular, the probe assembly (i.e. the flexible probe that is temporarily adhered to a rigid substrate/stiffener having an adhesive-filled wicking channel) may be attached to a rigid base piece, such as a glass slide, in the following manner. First, the tab of the insertion stiffener is adhered to the end of the glass slide with a secure adhesive such that the probe end is free. The connector with a temporary adhesive is adhered to the glass slide in another location, separate from the tab. The entire rigid piece is attached to the micromanipulator on the stereotaxic frame, aligning the probe with the insertion axis of the frame.

Next, as shown in the progression of FIGS. 21-24, the probe assembly is inserted into the target tissue to the desired depth. Once the probe is inserted into the desired location, the connector is carefully removed from the rigid piece (e.g. glass slide) attached to the micromanipulator, and transferred to an immobile region near the target tissue, as shown at FIG. 22. It may then he secured either temporarily or permanently to the target. Next, in FIG. 23, the flexible probe 42 is detached from the rigid stiffener 23. Phosphate buffered saline (PBS), is shown at 76 being applied at the insertion site, using a dropper or other means, to promote dissolution of the adhesive. The tab area above the tissue can be used to gage when the adhesive is beginning to dissolve. Sufficient time is allowed to fully dissolve the adhesive between the probe and stiffener. Different adhesives will take varying amounts of time to fully dissolve. Some testing will be required to determine this time. Then, as shown at FIG. 24, the stiffener 23 only is removed with the micromanipulator of the stereotaxic frame. With the connector detached from the frame and the adhesive fully dissolved, the stiffener can he extracted from the tissue by itself.

After the probe-stiffener assembly is inserted into tissue and the adhesive dissolves, the stiffener is extracted using the associated method previously described. Here we claim that using a variable extraction speed assists extraction of the stiffener with minimal displacement of the probe. The extraction sequence may consist of multiple steps with different speeds and accelerations at which the stiffener is drawn out of the tissue. The extraction speed profile may be controlled by a motorized micropositioner.

This concept describes a method of varying the extraction speed to achieve separation and extraction of the removable stiffener. After the dissolvable adhesive if dissolved, it is possible that there is static friction that would cause the probe to be dragged by the stiffener during extraction. To prevent this, the extraction is started with a relatively fast speed (e.g. 4 mm/second or faster) over a relatively small distance (several hundred microns). This fast motion will overcome static friction and cause minimal dragging of the probe. Then, the remainder of the extraction is completed with a relatively slow extraction speed (e.g. 0.2 mm/s).

Using the converse of this concept, we may take advantage of the static friction after initial insertion in order to make adjustments to its insertion depth. In this case, a relatively slow speed is used to nudge the probe and adjust its insertion depth before completely dissolving the removable adhesive and extracting of the removable stiffener.

Figure 20:
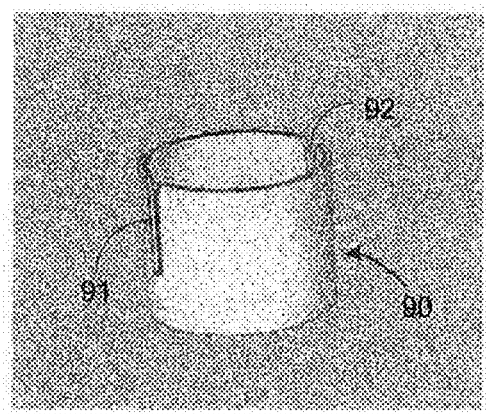
FIG. 20 is a perspective view of an example canula anchor used for anchoring an inserted probe while extracting the stiffener.
Figure 25:
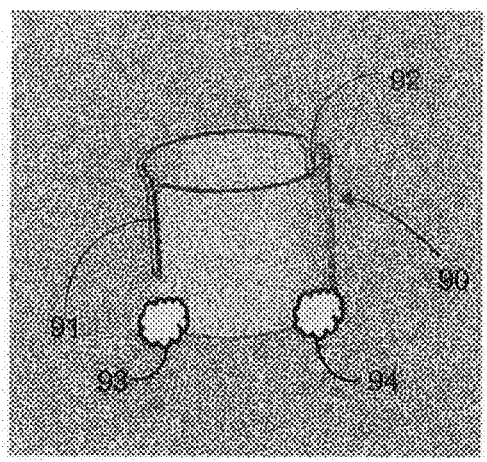
FIG. 25 is a perspective view of the example canula anchor of FIG. 20, shown anchored to a target in an example implantation process.
Figure 26:
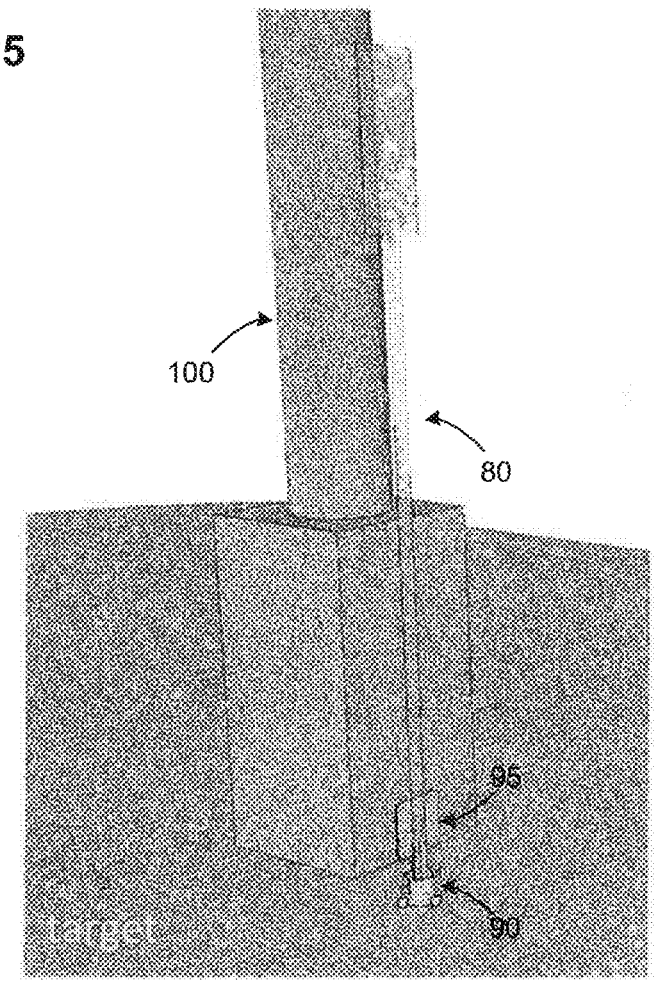
FIG. 26 is a perspective view of the stiffener-reinforced flexible electrode array probe assembly mounted on a micromanipulator of a stereotaxic frame, with the probe inserted.
Figure 29:
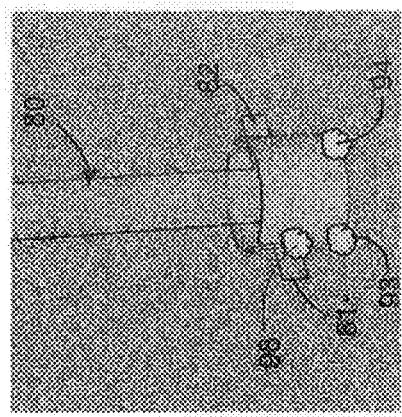
FIG. 29 is an enlarged perspective view of the inserted probe following FIG. 28, after extracting the stiffener.
Figure 28:
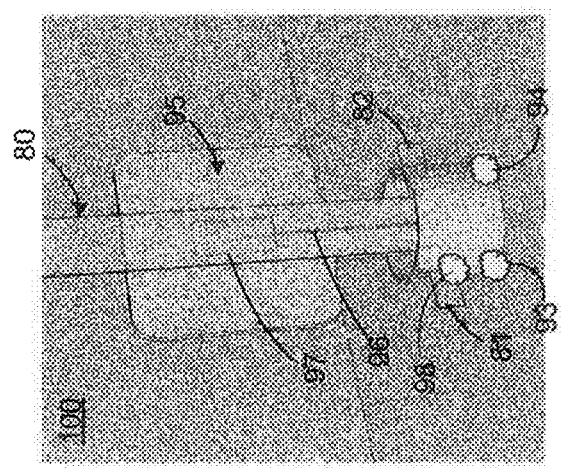
FIG. 28 is an enlarged perspective view of the inserted probe following FIG. 27, also showing adhering of an anchor arm of the probe to the canula anchor.
Figure 27:
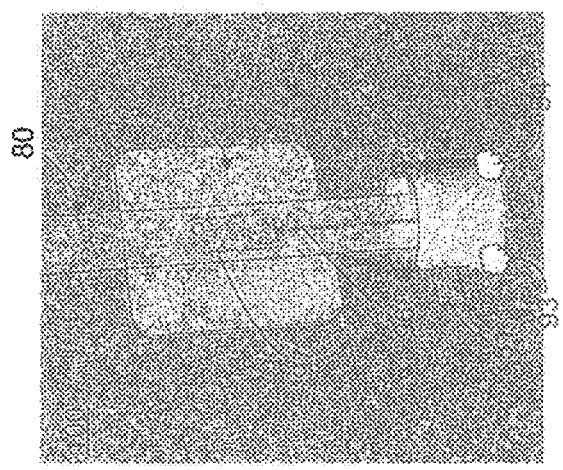
FIG. 27 is an enlarged perspective view of the inserted probe of FIG. 26.

Another example embodiment shown in FIGS. 25-29 utilize an anchor device to keep the flexible probe on the target when the stiffener is extracted. After insertion of the probe-stiffener assembly, the anchor will secure or anchor the flexible probe against motion while the stiffener is extracted. The anchoring component may be in contact with target tissue or surrounding areas, or it may be connected to a part of the stereotaxic frame that remains stationary while another moving part extracts the stiffener. The example anchoring process shown in FIGS. 19, 20 and 25-29 includes: providing an insertion section of the probe having anchor arms, such as the two arms or wings 81 and 82 shown in FIG. 19, and a canula-anchor 90. As shown in FIG. 20, the canula 90 is shown having two slots 91 and 92 for receiving the anchor arms 81 and 82 of the probe. As shown in FIG. 265, the canula-anchor 90 is first placed at insertion site and secured with cement, such as shown at 93, and 94. Next, the probe-stiffener assembly 80 and 95 in FIGS. 26 and 27 is inserted through the canula 90, aligning the wings into the slots. Cement or other adhesive is then applied to affix the wings 81 and 82 (only 81 shown affixed) to the canula, for securing the probe to the canula-anchor. The canula provides a surface to which to secure the probe while preventing cement from seeping along the probe edge and contacting the stiffener; extracting removable stiffener. It is notable that in this example, the canula is permanently located at the surgery site. Anchored in this manner, FIG. 29 shows the stiffener subsequently extracted. Stiffeners attached temporarily with dissolvable adhesive using the method previously described can be used to insert probes on which the active electrodes are contacting the stiffener during insertion (illustrated in FIG. 18). For example, planar probes with electrodes on both faces ("dual-sided probes") can be inserted using the method described since the stiffener will be subsequently removed to reveal the back side electrodes. Similarly, a single-sided probe may be inserted with the electrodes facing the removable stiffener if required by the surgical set up and the desired probe orientation.

It is also appreciated that the assembly process previously described which employs stiffeners with wicking channels may be used to attach probes with multiple shanks. Matching stiffeners have wicking channels along each shank. While a single shank probe is shown the figures to illustrate the features of the present invention, the present invention may also be realized and implemented as multi-shank probes. For such multi-shank embodiments, it is appreciated that the shanks are typically arranged in parallel and connected to a common base. Furthermore, each probe shank may have one or more contacts or exposed electrodes or leads.

Example Case

Assembly of Stiffener to Probe

An example method of assembly of a thin-film polymer probe to a silicon stiffener is next described:

A pellet of polyethylene glycol (PEG) of molecular weight 10,000 g/mol is first placed into a reservoir cavity at the tab section of the stiffener. The stiffener is then heated to 65° C. so that the PEG melts and wicks into the channel by capillary action. It is then cooled to room temperature to solidify. A flip chip bonder may be used next by placing the stiffener upside down on the base stage of the flip chip bonder. The stiffener is then picked up with the tool head. The elongated probe is positioned upside down on the base stage, i.e. the assembly base. Using the flip chip bonder, align the stiffener and the probe and then lower the stiffener and place it onto the probe. The base stage of the flip chip bonder should have a heating element to apply heat to the substrate. After placing the stiffener, the assembly is heated once again to 65° C. Two minutes is allowed for the PEG to remelt and begin to fill in the interface between the probe and stiffener. Cool to solidify. The assembly is turned over and inspected from the top. The assembly is reheated as needed to allow the PEG to completely fill the interface between the probe and the stiffener. This can be visually evaluated since the probe is transparent. Extra PEG is placed and melted onto the tab over the probe as reinforcement. Finally, the assembly is allowed to cool so that the PEG solidifies. At this point, the assembly is ready for surgical insertion.

Insertion and Extraction

This following is an example illustration of the insertion/extraction process of the present invention:

The probe-stiffener assembly may be mounted to a micromanipulator by adhering the back of the stiffener to the micromanipulator arm at the tab region. This may be done with double-sided tape or cement, (taking precautions not to contact the probe with adhesive). The connector end of the probe is temporarily secured to the micromanipulator with a small piece of adhesive putty such that it can be easily removed with low force. The probe assembly is then positioned over the target and the probe is inserted with the desired insertion speed. The connector end of the probe is immediately removed from the micromanipulator gently and positioned on a nearby surface. This is preferably done before the PEG begins to dissolve to avoid displacing the probe. Time is allowed (e.g. 10-15 minutes) for PEG to dissolve. During this time, phosphate buffered saline (PBS) is applied using a dropper around the tab and insertion point to dissolve any PEG that is above the target. Next, using either a manual or motorized micropositioner, the stiffener is extracted from the target (i.e. neural tissue) at approximately 2-5 mm/second. In the case of an actual surgery, normal procedures are continued by applying gel, silicone, and/or dental acrylic at the insertion site to secure and protect the probe.

Agarose Gel Test

A set up and procedure is described next to examine the extraction of the stiffener in a 0.6% agarose gel that approximates the bulk mechanical properties, pH, and salinity of brain tissue. Since the gel is nearly transparent through short distances, stiffener separation and probe displacement can be observed. The method includes: A solution of 0.6% agarose in phosphate buffered saline (PBS) is prepared. The solution is mixed at an elevated temperature to completely dissolve the agarose powder. The solution is poured into a shallow acrylic box; gel should be ¾"-1" deep. The gel is allowed to set at room temperature for an hour. Ensuring that the hardened gel is saturated with PBS so that it does not dry out, and the gel is heated to 37° C. The micromanipulator, box of agarose gel, and microscopic camera system are set up. A glass reference fiducial is inserted into the box of gel by sliding it between the gel and the side of the box. A dental pick is used to square the features on the reference fiducial to the field of view of the digital microscope. The probe assembly is mounted to the micromanipulator as previously described. The probe assembly is positioned over the gel about 1 mm behind the reference fiducial. The probe is inserted into the gel, using the camera to guide it to a desired depth in the field of view. The connector end of the probe is immediately moved to rest on a nearby surface. Any required adjustments to the camera image is made to focus on the probe (the reference fiducial features may be slightly out of focus). A snapshot of the probe location is taken. PEG is allowed to dissolve (this time may vary, and in fact may be a parameter to be tested). PBS is applied near the tab to dissolve PEG that is above the gel. Video capture is started if desired, and extraction of the stiffener is begun as previously described. When extraction is complete, a final snapshot of the probe location is taken. Image processing tools are used to compare the images before and after stiffener extraction. The features on the reference fiducial that are visible in the field of view are used to register (align) the images. The scale of the image is calibrated based on the size of known features on the probe. And the distance of probe displacement is measured.

Representative Results

The insertion technique of the present invention was used in conjunction with LLNL thin-film polyimide probes, which have passed ISO 10993 biocompatibility standards and are intended for chronic implantation. The thin-film polyimide probe along with a silicon stiffener that is approximately 10 mm long in the narrow region was used. This stiffener has one wicking channel running along its length. A pellet of solid PEG was placed into the reservoir of the tab, as seen through the camera on the flip chip bonder system. Once it was heated using the heater built into the base stage of the flip chip bonder, the PEG melted and began to wick into the channel. The camera view enabled monitoring of the wicking process until the PEG completely filled the channel, which took approximately an hour with PEG of molecular weight 10,000 g/mol. The PEG was then resolidified and the probe and stiffener were set up in the flip chip bonder. The final step in assembly is to add PEG to the tab region over the cable part of the probe, for extra reinforcement during handling. Since this area will not be inserted into the target, it is acceptable to have a larger volume of PEG here. This assembly method has been used to attach various shapes of probes to stiffeners, including multi-shank devices.

The in vitro agarose gel test has been used to qualitatively evaluate different parameters such as PEG molecular weight, time allowed for PEG to dissolve, and stiffener geometry. The test has also been used to quantify average probe displacement for a given probe/stiffener/adhesive configuration. Here we have shown an example of the latter. The test was performed using the insertion/extraction sequence of the present invention wherein the probe-stiffener assembly is inserted into the agarose gel, the connector end is moved to a nearby surface, the PEG is allowed to dissolve, and the stiffener is finally extracted leaving the probe in place. The experimental set up includes the probe-stiffener assembly attached to the micromanipulator arm and positioned over the gel. The reference fiducial was a small glass chip with an array of gold dots placed against the acrylic box in the field of view of the digital microscope.

The devices in this example were approximately 10 μm thick and 536 μm wide with eight 100-μm diameter electrodes. The traces consisted of a Ti—Au—Ti metal stack. The silicon stiffener was 200 μm wide, 6 mm long and 50 μm thick. The probe-stiffener assembly was inserted approximately 5 mm into the gel. The known pitch between the electrodes (200 μm) was used to calibrate the pixel size, since this dimension is less sensitive to variations in the fabrication process. The net probe displacement due to stiffener extraction was estimated to be 29±2 μm.

The method described here provides a well-controlled process to attach thin-film polymer probes to separate stiffeners with a biodissolvable adhesive. Also presented is the recommended surgical procedure to implement these removable stiffeners and a technique to validate the procedure in vitro for a given probe-stiffener configuration. Since the stiffener can be made arbitrarily rigid, the method can facilitate insertion of relatively long probes (>3 mm). As such, the insertion method is expected to be an enabling technology for applications in deep brain stimulation (DBS), spinal cord stimulation, and peripheral nerve interfaces.

The rigid stiffener with a wicking channel and the flip-chip based assembly process of the present invention are suitable for various materials and probe configurations. Geometrically, the stiffener does not have to match the probe footprint and could, for example, be narrower than the probe. The thickness of the stiffener may also vary. While stiffener made from silicon is described, other materials may be possible to achieve more desirable mechanical properties for certain applications. The assembly process is also suitable for other types of liquid adhesive. PEG is particularly easy to work with because of its ability to be solidified and remelted multiple times. In the case of other liquid adhesives that do not have this property, the assembly sequence may need to be modified. It is possible to use a different molecular weight for the PEG. A higher molecular weight will take longer to dissolve, which may be desirable during surgery. The contact area between the probe and stiffener will also affect the time needed to dissolve the adhesive after probe insertion. It is recommended that the probe-stiffener configuration with the chosen molecular weight be tested in vitro as described above to characterize the time required to dissolve the adhesive.

Modifications to the insertion/extraction procedure are in progress to make the process more robust. In particular, a very sensitive step is moving the connector end of the probe off of the micromanipulator onto a nearby surface. There is a risk in this step of disturbing the probe before it has been secured. It is also possible that the bend in the cable can cause stress on the inserted portion of the probe, leading to unintended displacement of the probe after stiffener extraction. Currently, these risks are mitigated by using a probe with a cable that is at least 2.5 cm long. However, it is desired that the insertion/extraction process be less dependent on the probe design. Modifications to the micromanipulator tool end or the addition of staging fixtures that can temporarily support the connector will likely allow more reliable extraction of the stiffener.

To date, the proposed method has been extended to actual animal surgery on several occasions to implant a probe into a rat cortex. After assembly, the probe and stiffener were sterilized together in EtO at room temperature. The insertion and extraction were performed with a micromanipulator attached to a stereotaxic frame and proceeded similarly to the sequence that was tested with agarose gel. Neural recordings were successfully obtained after recovery, demonstrating the viability of this method in real surgeries. Further histological testing is needed to verify probe placement in vivo and to fsquantify benefits of the flexible probe with a removable stiffener.

While particular operational sequences, materials, temperatures, parameters, and particular embodiments have been described and or illustrated, such are not intended to be limiting. Modifications and changes may become apparent to those skilled in the art, and it is intended that the invention be limited only by the scope of the appended claims.

We claim:

1. A method of assembling a rigid substrate onto a flexible device comprising:

providing a rigid substrate having an elongated section with a bonding side, and a narrow open groove channel formed on the bonding side adjacent an interface surface of the bonding side;

dispensing one or more adhesive pellets into the narrow open groove channel, and melting the one or more adhesive pellets into a liquid phase so that the liquid-phase adhesive wicks along and completely fills the narrow open groove channel by capillary action; and positioning a flexible device adjacent the interface surface of the rigid substrate so as to wick adhesive from the narrow open groove channel to a space in-between the flexible device and the interface surface of the rigid substrate and adhere the flexible device to the interface surface of the bonding side of the elongated section of the rigid substrate.

2. The method of claim 1, further comprising heating the adhesive to improve wicking by decreasing its viscosity.

3. A method of assembling a rigid substrate onto a flexible device comprising: providing a rigid substrate having an elongated section with a bonding side, and a narrow open groove channel formed on the bonding side adjacent an interface surface of the bonding side, wherein the rigid substrate has a tab section connected to the elongated section, and a reservoir cavity formed on the tab section that is in fluidic communication with the narrow open groove channel; dispensing one or more adhesive pellets into the reservoir cavity of the tab section, and melting the one or more adhesive pellets into a liquid phase so that the liquid-phase adhesive wicks along and completely fills the reservoir cavity and the narrow open groove channel by capillary action; and positioning a flexible device adjacent the interface surface of the rigid substrate so as to wick adhesive from the narrow open groove channel to a space in-between the flexible device and the interface surface of the rigid substrate and adhere the flexible device to the interface surface of the adhesive filled bonding side of the elongated section of the rigid substrate.

4. The method of claim 3, wherein the reservoir cavity is an open cavity having a receiving end.

5. A method of assembling a rigid substrate onto a flexible device comprising:

providing a rigid substrate having an elongated section, and a narrow open groove channel formed on a bonding side of the elongated section;

dispensing a liquid adhesive into the narrow open groove channel so that the adhesive is wicked along and fills the narrow open groove channel by capillary action, wherein the step of dispensing the liquid adhesive into the narrow open groove channel includes: dispensing one or more adhesive pellets into the narrow open groove channel, and melting the one or more adhesive pellets into a liquid phase so that the liquid-phase adhesive wicks along and fills the narrow open groove channel;

re-solidifying the liquid-phase adhesive into a solid phase in the narrow open groove channel; and adhering the adhesive-filled bonding side of the elongated section of the rigid substrate to a flexible device, wherein the adhering step includes aligning the rigid substrate with the flexible device, followed by re-melting the solid-phase adhesive into the liquid phase to conformably contact the flexible device, and followed by re-solidifying the liquid-phase adhesive so as to adhere the adhesive-filled bonding side of the elongated section of the rigid substrate to the flexible device.

\* \* \* \* \*